United States Patent
Caltabiano et al.

(10) Patent No.: US 9,522,129 B2
(45) Date of Patent: *Dec. 20, 2016

(54) PHARMACEUTICAL COMBINATION

(71) Applicant: VELICEPT THERAPEUTICS, INC., Malvern, PA (US)

(72) Inventors: Stephen Caltabiano, King of Prussia, PA (US); Eliot Ohlstein, Glenmoore, PA (US); Stewart McCallum, King of Prussia, PA (US)

(73) Assignee: Velicept Therapeutics, Inc., Malvern, PA (US)

( * ) Notice: Subject to any disclaimer, the term of this patent is extended or adjusted under 35 U.S.C. 154(b) by 507 days.

This patent is subject to a terminal disclaimer.

(21) Appl. No.: 13/762,563

(22) Filed: Feb. 8, 2013

(65) Prior Publication Data

US 2013/0172277 A1    Jul. 4, 2013

Related U.S. Application Data

(63) Continuation-in-part of application No. 13/196,068, filed on Aug. 2, 2011, now Pat. No. 8,642,661.

(60) Provisional application No. 61/370,171, filed on Aug. 3, 2010, provisional application No. 61/596,893, filed on Feb. 9, 2012.

(51) Int. Cl.
| | |
|---|---|
| *A61K 31/135* | (2006.01) |
| *A01N 33/02* | (2006.01) |
| *A01N 33/00* | (2006.01) |
| *A61K 31/13* | (2006.01) |
| *A61K 31/16* | (2006.01) |
| *A01N 43/04* | (2006.01) |
| *A61K 31/70* | (2006.01) |
| *A61K 31/216* | (2006.01) |
| *A61K 31/7024* | (2006.01) |
| *A61K 31/196* | (2006.01) |
| *A61K 31/426* | (2006.01) |
| *A61K 45/06* | (2006.01) |
| *A61K 31/137* | (2006.01) |
| *A61K 31/357* | (2006.01) |
| *A61K 31/4725* | (2006.01) |
| *A61K 31/351* | (2006.01) |

(52) U.S. Cl.
CPC .......... *A61K 31/216* (2013.01); *A61K 31/137* (2013.01); *A61K 31/196* (2013.01); *A61K 31/351* (2013.01); *A61K 31/357* (2013.01); *A61K 31/426* (2013.01); *A61K 31/4725* (2013.01); *A61K 31/7024* (2013.01); *A61K 45/06* (2013.01)

(58) Field of Classification Search
CPC    A61K 31/216; A61K 31/7024; A61K 31/196; A61K 31/426; A61K 45/06
USPC ................. 514/646, 579, 25, 659
See application file for complete search history.

(56) References Cited

U.S. PATENT DOCUMENTS

| | | |
|---|---|---|
| 4,478,849 A | 10/1984 | Ainsworth et al. |
| 4,772,631 A | 9/1988 | Holloway et al. |
| 6,069,176 A | 5/2000 | Tsuchiya et al. |
| 6,251,925 B1 | 6/2001 | Donaldson et al. |
| 6,395,762 B1 | 5/2002 | Fobare et al. |
| 6,444,685 B1 | 9/2002 | Sum et al. |
| 6,451,814 B1 | 9/2002 | Ashwell et al. |
| 7,022,716 B2 | 4/2006 | Hu et al. |
| 7,034,053 B2 | 4/2006 | Deaton et al. |
| 7,425,639 B2 | 9/2008 | Cooke et al. |
| 7,709,677 B2 | 5/2010 | Cooke et al. |
| 8,017,613 B2 | 9/2011 | Scilimati et al. |
| 8,247,415 B2 | 8/2012 | Berger et al. |
| 8,354,403 B2 | 1/2013 | Edmondson et al. |
| 8,399,480 B2 | 3/2013 | Berger et al. |
| 8,642,661 B2 * | 2/2014 | Caltabiano et al. .......... 514/646 |
| 2004/0122014 A1 | 6/2004 | Mammen et al. |
| 2005/0101607 A1 | 5/2005 | Michel et al. |
| 2005/0154041 A1 | 7/2005 | Michel et al. |
| 2005/0261328 A1 | 11/2005 | Wienrich et al. |
| 2005/0261369 A1 | 11/2005 | Mehlburger et al. |
| 2006/0084700 A1 | 4/2006 | Michel |
| 2007/0078181 A1 | 4/2007 | Michel |
| 2009/0253705 A1 | 10/2009 | Berger et al. |
| 2010/0240697 A1 | 9/2010 | Suzuki et al. |
| 2010/0286275 A1 | 11/2010 | Zhang |
| 2011/0028461 A1 | 2/2011 | Berger et al. |
| 2011/0081246 A1 | 4/2011 | Aynsley et al. |
| 2012/0035118 A1 | 2/2012 | Caltabiano et al. |
| 2012/0053181 A1 | 3/2012 | Lin et al. |

(Continued)

FOREIGN PATENT DOCUMENTS

| | | |
|---|---|---|
| CA | 2507343 A1 | 7/2005 |
| EP | 0400519 A | 12/1990 |

(Continued)

OTHER PUBLICATIONS

Definition of "compound" and "composition" from the Grant & Hackh's Chemical Dictionary (1987) p. 148, McGraw-Hill, Inc.*
Hicks, Alexander, et al. "GW427353 (solabegron), a novel, selective beta(3)-Adrenergic receptor agonist, evokes blader relaxation and increases micturition reflex threshold in the dog", Journal of Pharmacology and Experimental Therapeutics, vol. 323, No. 1, Oct. 2007, pp. 202-209, URL, XP000002658787, ISSN: 0022-3565.

(Continued)

*Primary Examiner* — Scarlett Goon
(74) *Attorney, Agent, or Firm* — Pepper Hamilton LLP

(57) ABSTRACT

Pharmaceutical combinations comprising a beta-3 adrenergic receptor agonist and a muscarinic receptor antagonist, and methods for their use are disclosed. Methods of using the pharmaceutical combinations for the treatment of one or more symptoms associated with overactive bladder, for example, frequency of urgency, nocturia, and urinary incontinence, are also disclosed.

16 Claims, 8 Drawing Sheets

(56) References Cited

U.S. PATENT DOCUMENTS

| | | | |
|---|---|---|---|
| 2012/0142725 | A1 | 6/2012 | Van Charldorp et al. |
| 2012/0202819 | A1 | 8/2012 | Edmondson et al. |
| 2012/0225886 | A1 | 9/2012 | Edmondson et al. |
| 2012/0258963 | A1 | 10/2012 | Berger et al. |
| 2013/0053403 | A1 | 2/2013 | Berger et al. |
| 2013/0150402 | A1 | 6/2013 | Suzuki et al. |
| 2013/0172277 | A1 | 7/2013 | Caltabiano et al. |

FOREIGN PATENT DOCUMENTS

| | | |
|---|---|---|
| EP | 0455006 A | 11/1991 |
| EP | 0543662 A | 5/1993 |
| EP | 1 258 253 A1 | 11/2002 |
| EP | 1967202 A1 | 9/2008 |
| EP | 2216021 | 8/2010 |
| WO | WO 95/33724 A | 12/1995 |
| WO | WO 99/65877 A1 | 12/1999 |
| WO | WO 01/54728 A1 | 8/2001 |
| WO | 03 024483 A1 | 3/2003 |
| WO | WO 2004/041806 A1 | 5/2004 |
| WO | WO-200441806 A2 | 5/2004 |
| WO | WO-200447838 A2 | 6/2004 |
| WO | 2008 121268 A1 | 10/2008 |
| WO | 2009/057685 A1 † | 5/2009 |
| WO | 2010 118291 A2 | 10/2010 |
| WO | 2011 043942 A1 | 4/2011 |
| WO | WO 2012/018773 A1 | 2/2012 |
| WO | WO 2013/119910 A1 | 8/2013 |
| WO | WO 2016/004056 A1 | 1/2016 |

OTHER PUBLICATIONS

International Search Report mailed Sep. 26, 2011, International Application No. PCT/US2011/046208 in the name of Altherx, Inc.
Otsuka, et al. "Combination Effect of B3-Adrenoceptor Agonist and Muscarinic Receptor Antagonist on Human Detrusor Muscle Relaxation in Vitro." International Continence Society Meeting, Oct. 2012, pp. 894-895.
Gillespie, et al. "Modulation of non-voiding activity by the muscarinergic antagonist tolterodine and the ? 3 -adrenoceptor agonist mirabegron in conscious rats with partial outflow obstruction." BJU International 110, E132-142. (2012).
Rackley et al. "Nighttime Dosing with Tolterodine Reduces Overactive Bladder-Related Nocturnal Micturitions in Patients with Overactive Bladder and Nocturia", Urology 67: 731-736. (2006).
Abrams, et al. "Combination treatment with mirabegron and solifenacin in patients with overactive bladder (OAB) efficacy results from a phase 2 study (Symphony)". AUA Annual Meeting, May 4-May 8, 2013, San Diego, CA. <<http://www.aua2013.org/abstracts/archive/abstracts_MP72.cfm>> Last accessed Sep. 17, 2013.
Information about Related Patents and Patent Applications, see section 6 of the accompanying Information Disclosure Statement Letter, which concerns Related Patents and Patent Applications.
Biers et al., The effects of a new selective $\beta_3$-adrenoceptor agonist (GW427353) on spontaneous activity and detrusor relaxation in human bladder, *Journal Compilation, 2006 BJU International* (2006), 98:1310-1314.
Grudell et al. "Dose-response effect of a Beta-3-adrenergic Receptor Agonist, Solabegron, on Gastrointestinal Transit, Bowel Function, and Somatostatin Levels in Health" May 1, 2008, Am. J. Physiol.—Gastro. Liver Physiol. 294(5):G1114-G1119.
International Search Report and Written Opinion for PCT/US2013/025285 dated Mar. 25, 2013.
International Search Report and Written Opinion for PCT/US2015/038583 dated Sep. 17, 2015.
Irwin et al., Prevalence, Severity, and Symptom Bother of Lower Urinary Tract Symptoms among Men in the EPIC Study: Impact of Overactive Bladder, *European Urology* (Mar. 3, 2009), 56:14-20.
NCT00501267: "A Study to Test the Interaction of Two Medications for the Treatment of Overactive Bladder" available at https://clinicaltrials.gov/ct2/show/NCT00501267?term=NCT00501267&rank=1 (as retrieved on Feb. 15, 2016).
Ohlstein et al., A Multicenter, Double-blind, Randomized, Placebo-controlled Trial of the β3-Adrenoceptor Agonist Solabegron for Overactive Bladder, *European Urology* (Jun. 5, 2012), 62:834-840.
Singapore Search Report for SG 11201404776P dated Jul. 8, 2015.
Product Label for Myrbetriq™ (mirabegron) (Jun. 2012).†
Product Label for VESIcare® (solifenacin succinate) (Apr. 2010).†

\* cited by examiner
† cited by third party

Effects of antimuscarinics alone on EFS-induced contractions in the different groups (% inhibition from basal)

| | Vehicle | Oxybutynin 10 nM | Tolterodine 10 nM | Solifenacin 10 nM |
|---|---|---|---|---|
| CL-316,243 | 5.87 ± 0.22 % (n=2) | 29.39 ± 14.50 % (n=2) | 39.10 ± 4.99 % (n=5) | 10.73 ± 2.00 % (n=5) |
| Solabegron | 6.75 ± 1.36 % (n=5) | 18.96 ± 1.83 % (n=5) | 22.70 ± 4.75 % (n=5) | 10.40 ± 1.38 % (n=5) |
| Mirabegron | 9.06 ± 1.65 % (n=5) | 17.85 ± 1.05 % (n=5) | 32.29 ± 3.16 % (n=5) | 9.51 ± 4.02 % (n=5) |

FIGURE 2

$E_{max}$ and $pIC_{50}$ values

|  | Vehicle | Oxybutynin 10 nM | Tolterodine 10nM | Solifenacin 10 nM |
|---|---|---|---|---|
| CL-316,243 | $E_{max}$ = 71.0 ± 3.9 %<br>$pIC_{50}$ = 8.0 ± 0.2 | $E_{max}$ = 89.9* ± 3.4 %<br>$pIC_{50}$ = 8.7* ± 0.2 | $E_{max}$ = 91.3* ± 1.5 %<br>$pIC_{50}$ = 8.4 ± 0.2 | $E_{max}$ = 70.9 ± 1.5 %<br>$pIC_{50}$ = 8.1 ± 0.1 |
| Solabegron | $E_{max}$ = 48.3 ± 3.3 %<br>$pIC_{50}$ = 6.8 ± 0.3 | $E_{max}$ = 63.0* ± 2.7 %<br>$pIC_{50}$ = 7.3* ± 0.2 | $E_{max}$ = 67.1* ± 2.6 %<br>$pIC_{50}$ = 7.5* ± 0.1 | $E_{max}$ = 60.6* ± 2.1 %<br>$pIC_{50}$ = 7.0 ± 0.1 |
| Mirabegron | $E_{max}$ = 71.5 ± 4.9 %<br>$pIC_{50}$ = 5.8 ± 0.1 | $E_{max}$ = 68.2 ± 2.3 %<br>$pIC_{50}$ = 6.1* ± 0.1 | $E_{max}$ = 81.9 ± 3.1 %<br>$pIC_{50}$ = 6.5* ± 0.2 | $E_{max}$ = 68.5 ± 3.2 %<br>$pIC_{50}$ = 6.1* ± 0.1 |

(*) $p < 0.05$ versus vehicle group

FIGURE 7

$E_{max}$ and $IC_{50}$ values

| | Vehicle | Oxybutynin 10 nM | Tolterodine 10 nM | Solifenacin 10 nM |
|---|---|---|---|---|
| CL-316,243 | $E_{max}$ = 68.6 ± 3.0 % <br> $IC_{50}$ = 7.36 nM | $E_{max}$ = 84.7* ± 2.7 % <br> $IC_{50}$ = 1.91* nM | $E_{max}$ = 91.3* ± 1.5 % <br> $IC_{50}$ = 4.17 nM | $E_{max}$ = 71.2 ± 1.4 % <br> $IC_{50}$ = 8.85 nM |
| Solabegron | $E_{max}$ = 48.3 ± 3.3 % <br> $IC_{50}$ = 0.14 µM | $E_{max}$ = 63.0* ± 2.7 % <br> $IC_{50}$ = 0.05* µM | $E_{max}$ = 67.1* ± 2.6 % <br> $IC_{50}$ = 0.03* µM | $E_{max}$ = 60.6* ± 2.1 % <br> $IC_{50}$ = 0.09 µM |
| Mirabegron | $E_{max}$ = 71.5 ± 4.9 % <br> $IC_{50}$ = 1.71 µM | $E_{max}$ = 68.2 ± 2.3 % <br> $IC_{50}$ = 0.87* µM | $E_{max}$ = 81.9 ± 3.1 % <br> $IC_{50}$ = 0.33* µM | $E_{max}$ = 68.5 ± 3.2 % <br> $IC_{50}$ = 0.77* µM |

(*) $p < 0.05$ versus vehicle group

FIGURE 8

PHARMACEUTICAL COMBINATION

CROSS-REFERENCE TO RELATED APPLICATIONS

The present application is a Continuation-in-Part under 35 U.S.C. 120 of U.S. patent application Ser. No. 13/196,068, filed on Aug. 2, 2011, which claims the benefit of priority under 35 U.S.C. 119(e) of U.S. Provisional Application 61/370,171 filed on Aug. 3, 2010. The present application also claims the benefit of priority under 35 U.S.C. 119(e) of U.S. Provisional Application No. 61/596,893, filed on Feb. 9, 2012. The entire disclosures of all of the above applications are incorporated herein by reference.

FIELD OF THE INVENTION

The present invention relates to pharmaceutical combinations and methods for their use. In particular, the invention relates to pharmaceutical combinations comprising a beta-3 adrenergic receptor agonist and a muscarinic acetylcholine receptor antagonist (hereinafter referred to as "muscarinic receptor antagonist" or "antimuscarinic"), and to methods of using such combinations in the treatment of one or more symptoms associated with overactive bladder, for example, frequency of urgency, frequency of mictruitions, nocturia, and urinary incontinence.

BACKGROUND OF THE INVENTION

The International Continence Society (ICS) has defined overactive bladder (OAB) as a symptom complex of urgency, with or without urge incontinence, accompanied by frequency and nocturia. The symptoms of overactive bladder are usually associated with involuntary contractions of the detrusor (bladder) muscle thus creating a state of bladder hyperactivity. OAB is commonly classified into subtypes including neurogenic, idiopathic, and outlet obstruction. Neurogenic DAB is attributed to coexisting neurological conditions such as Parkinson's disease, multiple sclerosis, spinal cord injury or stroke. The underlying pathophysiology is the interruption of the otherwise orderly control of micturition, resulting in the symptom complex described above. The cause of idiopathic OAB is not as well defined; alterations in signalling within the bladder have been implicated. Finally, OAB may be associated with anatomical changes in the lower urinary tract, for example, in patients with bladder outlet obstruction, which may be the result of an enlarged prostate gland. Overall, the incidence of OAB increases with age. The ratio of men to women affected depends on the age group, but in general women tend to be more affected than men. OAB represents a significant quality of life burden to patients.

Muscarinic receptor antagonists (also known as antimuscarinics or anticholinergics) such as Detrol® LA (tolterodine), Ditropan XL® (oxybutynin), and Vesicare® (solifenacin succinate) currently represent the major pharmacological options approved and marketed for the treatment of OAB. Antimuscarinics are believed to reduce bladder overactivity by inhibiting bladder smooth muscle contractility. Physicians and patients remain unsatisfied with the current therapies and desire medicines with improved efficacy and tolerability. In particular there is an unacceptably high incidence of side effects, including dry mouth and constipation associated with these medications. Also, current medications do not adequately treat urgency, one of the most bothersome symptoms of OAB.

Accordingly, there remains a need for new medicines and methods of treatment that offer improved efficacy and tolerability in the treatment of symptoms associated with overactive bladder, above and beyond the currently available therapies.

SUMMARY OF THE INVENTION

A method of treating one or more symptoms associated with overactive bladder using a new synergistic treatment combination has now been discovered. The treatment combination according to the invention comprises a beta-3 adrenergic receptor agonist and a muscarinic receptor antagonist. The inventors have shown that this combination has unexpectedly increased potency and efficacy, and is useful for the treatment of one or more symptoms associated with OAB.

Accordingly, the invention encompasses treatment combinations comprising (i) a therapeutically effective amount of a beta-3 adrenergic receptor agonist, and (ii) a therapeutically effective amount, or a sub-therapeutically effective amount, of a muscarinic receptor antagonist, the combination being useful for relieving one or more symptoms associated with overactive bladder (OAB) in a synergistic manner, versus the individual components (i) and (ii). The symptoms associated with overactive bladder are selected from the group consisting of frequency of urgency, frequency of mictruitions, nocturia, and urinary incontinence. The invention also encompasses methods of treating one or more symptoms associated with overactive bladder in a mammal using (i) and (ii), either in a single dosage form or separately.

Use of the combinations for the treatment of one or more symptoms associated with overactive bladder, use of the combinations in medical therapy, and use of the combinations in the preparation of a medicament for the treatment of one or more symptoms associated with overactive bladder are also provided.

The beta-3 adrenergic receptor agonist can comprise a compound selected from the group consisting of solabegron. CL-316,243, mirabegron, pharmaceutically acceptable salts thereof, pharmaceutically acceptable solvates thereof, and pharmaceutically acceptable salts solvated with pharmaceutically acceptable solvents thereof.

The muscarinic receptor antagonist can comprise a compound selected from the group consisting of oxybutynin, tolterodine, solifenacin, pharmaceutically acceptable salts thereof, pharmaceutically acceptable solvates thereof, and pharmaceutically acceptable salts solvated with pharmaceutically acceptable solvents thereof.

In a preferred embodiment the combination comprises (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

Another aspect of the invention is directed to a method of treating one or more symptoms associated with overactive bladder in a mammal, comprising administering to the mammal (i) a therapeutically effective amount of a beta-3 adrenergic receptor agonist; and (ii) a therapeutically effective amount, or a sub-therapeutically effective amount of a muscarinic receptor antagonist.

In one embodiment of the method, the beta-3 adrenergic receptor agonist comprises a compound selected from the group consisting of solabegron, CL-316,243, mirabegron, pharmaceutically acceptable salts thereof, pharmaceutically acceptable solvates thereof, and pharmaceutically acceptable salts solvated with pharmaceutically acceptable solvents thereof.

In a further embodiment of the method, the muscarinic receptor antagonist comprises oxybutynin, tolterodine, solifenacin, pharmaceutically acceptable salts thereof, pharmaceutically acceptable solvates thereof, and pharmaceutically acceptable salts solvated with pharmaceutically acceptable solvents thereof.

In a preferred embodiment, the method of treating one or more symptoms associated with overactive bladder in a mammal, comprises administering to the mammal (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof.

The method can comprise co-administration of components (i) and (ii). In one embodiment, components (i) and (ii) are contained in a single dosage form. In another embodiment, co-administration comprises administering together the separately formulated components (i) and (ii).

The method can also comprise separate administration of components (i) and (ii). When administered separately there can be a time delay between the administration of components (i) and (ii).

In a preferred embodiment, the salt of solabegron comprises the hydrochloride salt.

Another embodiment is directed to a pharmaceutical composition comprising the combination of components (i) and (ii), and further comprising one or more pharmaceutically acceptable carriers, diluents, or excipients.

A further embodiment is directed to a method of treating one or more symptoms associated with overactive bladder in a mammal, comprising the step of administering to a mammal in need thereof, a therapeutically effective amount of the above-identified combination of components (i) and (ii).

Another embodiment is directed to a method in which component (i) comprises solabegron, wherein component (i) further comprises the compound of Formula (III)

BRIEF DESCRIPTION OF THE DRAWINGS

FIG. 2 shows the effects on EFS-induced contractions (% inhibition from basal) of various antimuscarinics in combination with various beta-3 adrenoceptor agonists.

FIG. 7 shows $E_{max}$ and $pIC_{50}$ values of various beta-3 adrenoceptor agonists, either alone (vehicle) or in the presence of 10 nM of various antimuscarinics.

FIG. 8 shows $E_{max}$ and $IC_{50}$ values of various beta-3 adrenoceptor agonists, either alone (vehicle) or in the presence of 10 nM of various antimuscarinics.

DETAILED DESCRIPTION OF THE INVENTION

Figure 1:
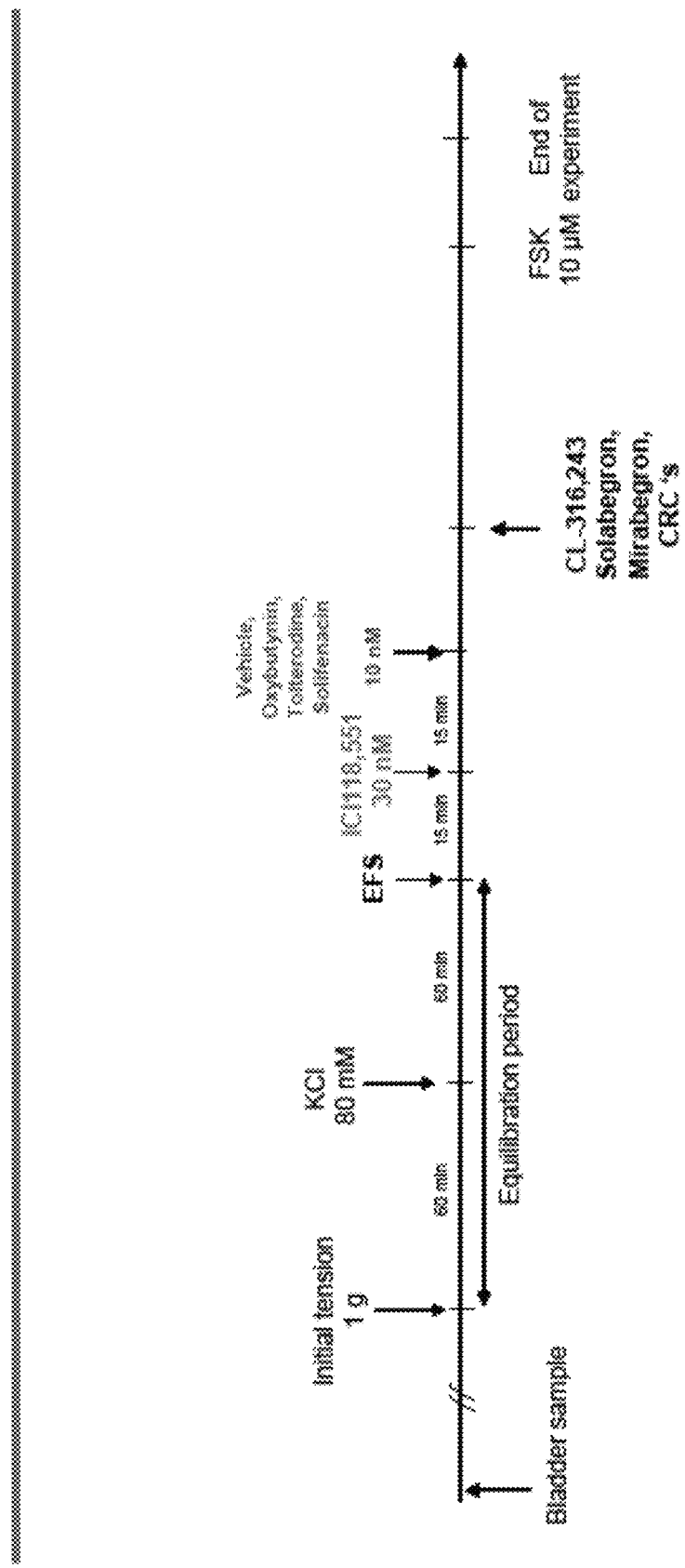
FIG. 1 shows a graph of the Experimental protocol of Example 3.
Figure 3:
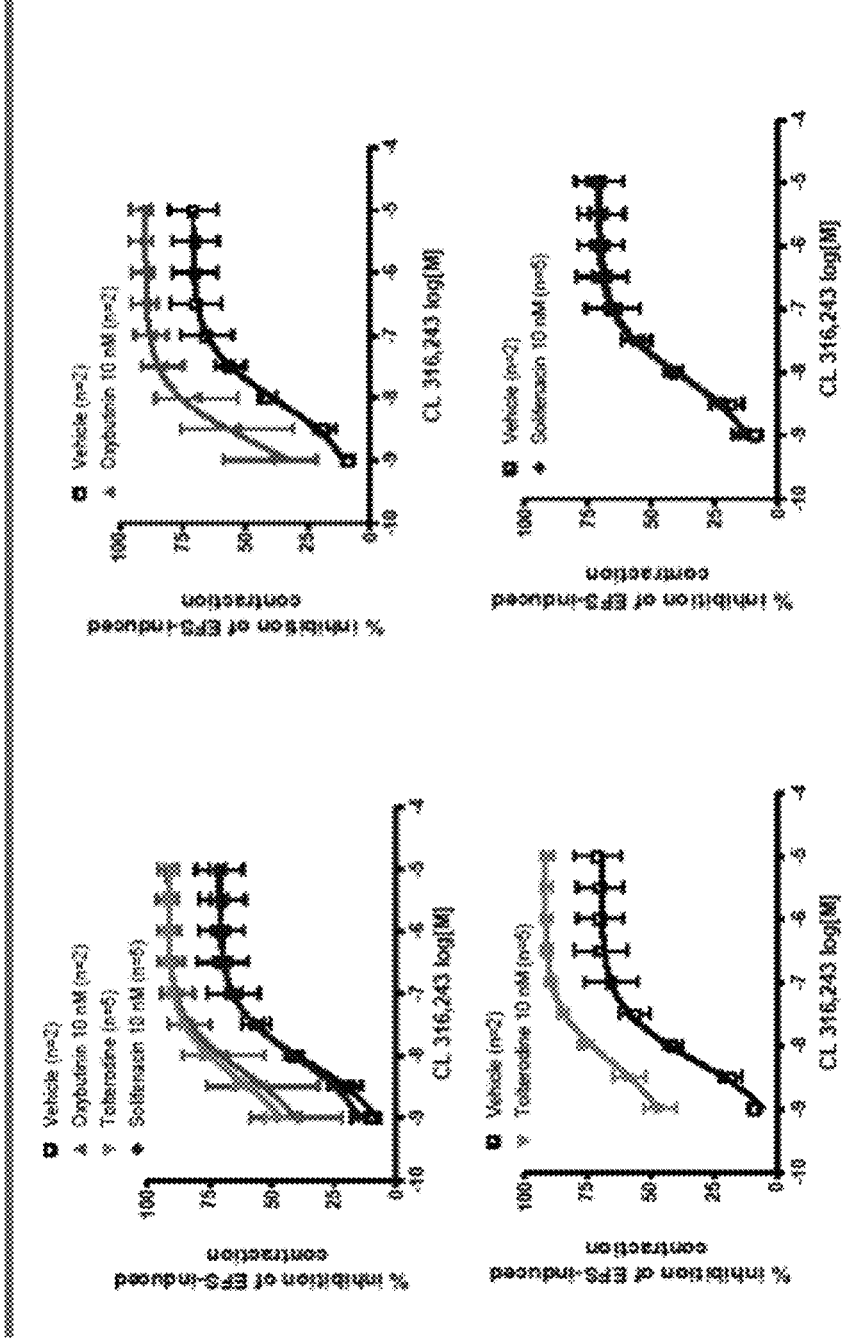
FIG. 3 displays the effects of various antimuscarinics on CL-316,243 inhibition of EFS-induced contractions of rat isolated urinary bladder.
Figure 4:
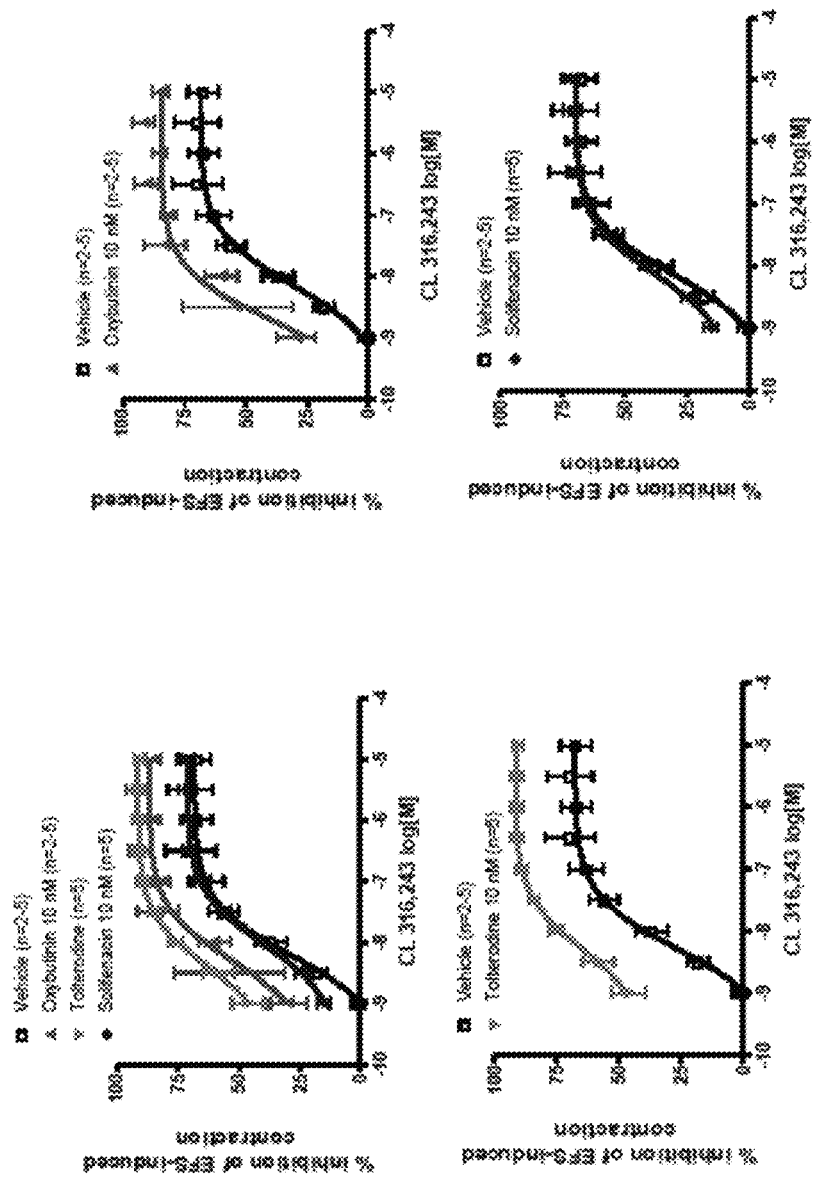
FIG. 4 displays the effects of antimuscarinics on CL-316, 243 inhibition of EFS induced contractions of rat isolated urinary bladder, including previous results.
Figure 5:
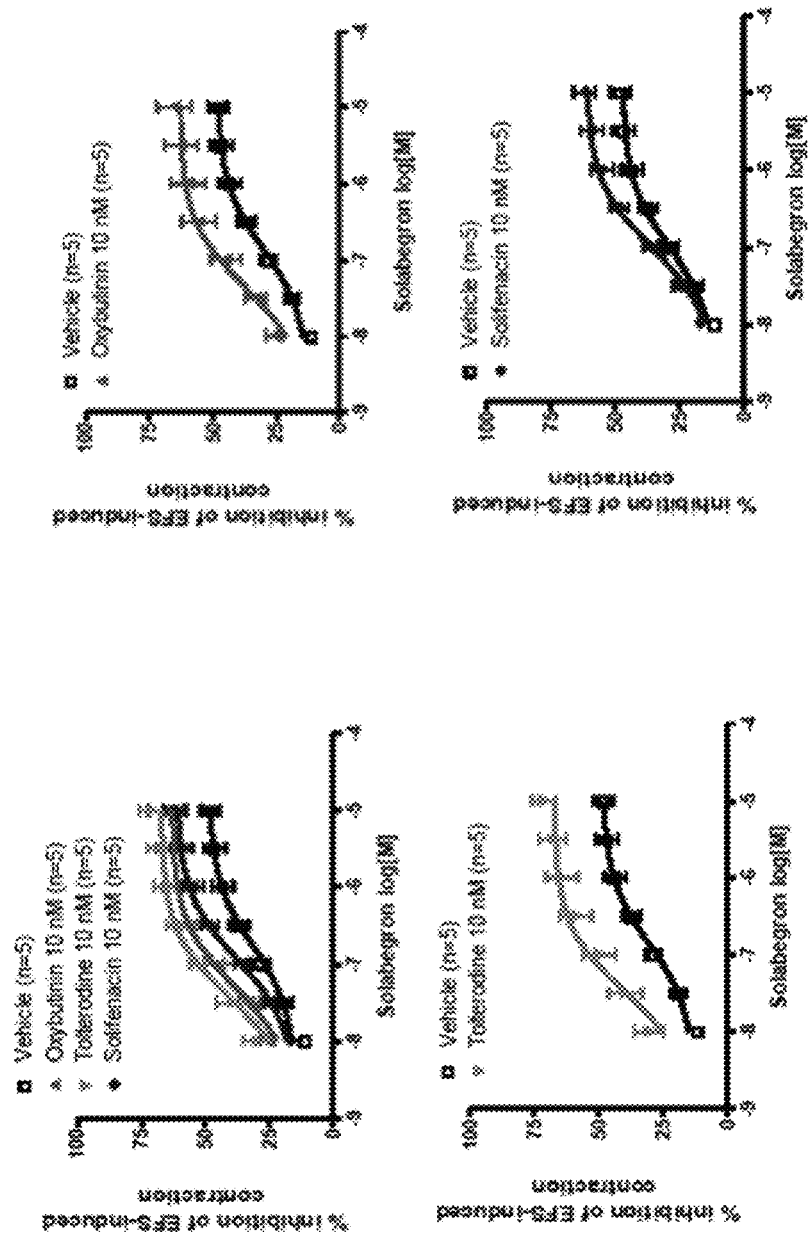
FIG. 5 displays the effects of various antimuscarinics on solabegron inhibition of EFS-induced contractions of rat isolated urinary bladder.
Figure 6:
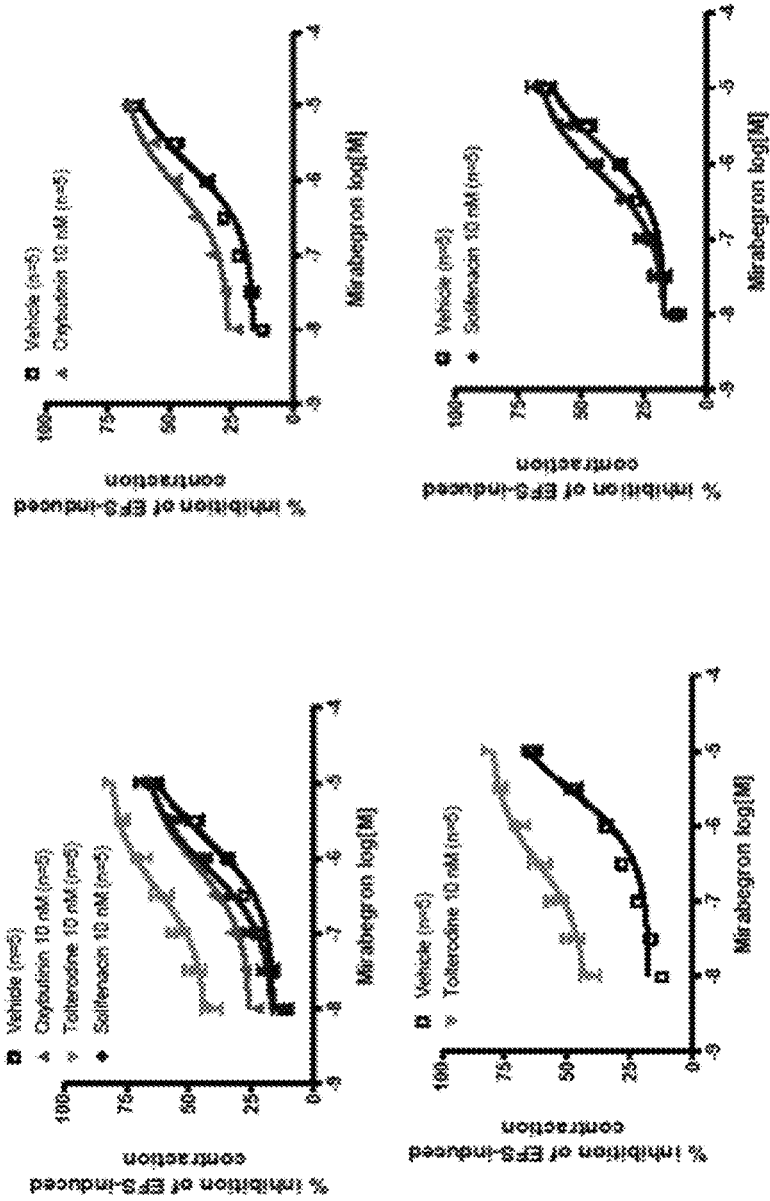
FIG. 6 displays the effects of various antimuscarinics on mirabegron inhibition of EFS-induced contractions of rat isolated urinary bladder.

Unexpectedly, new synergistic drug combinations have been discovered which are useful in treating one or more symptoms associated with OAB. These combinations comprise (i) a beta-3 adrenergic receptor agonist, and (ii) a muscarinic receptor antagonist. It has been demonstrated that these combinations have surprisingly increased potency and efficacy, and are useful for the treatment of at least one symptom associated with OAB.

Accordingly, one embodiment of the invention encompasses treatment combinations comprising (i) a therapeutically effective amount of a beta-3 adrenergic receptor agonist, and (ii) a therapeutically effective amount, or a sub-therapeutically effective amount, of a muscarinic receptor antagonist. A sub-therapeutically effective dose of the muscarinic antagonist can be used due to the synergy of the combination. In particular, one embodiment encompasses a synergistic combination comprising:

(i) a therapeutically effective amount of a beta-3 adrenergic receptor agonist; and
(ii) a therapeutically effective amount, or a sub-therapeutically effective amount, of a muscarinic receptor antagonist, Formula (III)

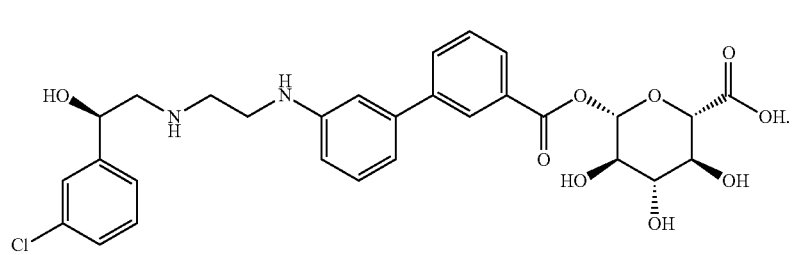

the combination being useful for relieving one or more symptoms associated with overactive bladder (OAB) in a synergistic manner, versus the individual components (i) and (ii).

A further embodiment encompasses a method of treating one or more symptoms associated with OAB in a mammal comprising administering to the mammal:
(i) a therapeutically effective amount of a beta-3 adrenergic receptor agonist; and
(ii) a therapeutically effective amount, or a sub-therapeutically effective amount, of a muscarinic receptor antagonist, wherein the administration of the combination of both (i) and (ii) is effective for relieving one or more symptoms associated with overactive bladder (OAB) in a synergistic manner, versus the individual components (i) and (ii).

Thus, in one embodiment, the combinations of (i) and (ii) can be used for the treatment of one or more symptoms associated with overactive bladder. In another embodiment, the combinations of (i) and (ii) can be used in medical therapy. In a further embodiment the combinations of (i) and (ii) can be used in the preparation of a medicament for the treatment of one or more symptoms associated with OAB.

In a further embodiment, the compounds (i) and (ii), or pharmaceutical preparations containing them, can be administered separately, with or without a time delay, for the treatment of one or more symptoms associated with OAB.

As used herein, the term "effective amount" means that amount of a drug or pharmaceutical agent, or that amount of a combination of drugs or pharmaceutical agents that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder, as was known in the art as of the date of the present invention. The term also includes within its scope amounts effective to enhance normal physiological function, as was known in the art as of the date of the present invention.

Accordingly, the term "sub-therapeutically effective amount" indicates any amount of the muscarinic receptor antagonist which is not therapeutically effective or is minimally therapeutically effective alone, as was known in the art as of the date of the present invention, but which in combination with a therapeutically effective amount of the beta-3 adrenergic receptor agonist, demonstrates a synergistic therapeutic effect. In particular embodiments of the presently claimed combinations and methods, a lower dose (sub-therapeutic dose) of the antimuscarinic agent can be used to produce superior efficacy of the combination due to the synergy of the two compounds, while avoiding or minimizing the side effects of the antimuscarinic agent.

In a further embodiment of the invention, either the beta-3 adrenergic receptor agonist or the muscarinic receptor antagonist, or both, can be combined in sub-therapeutically effective amounts, as defined in the art for the single agents as of the date of the present invention, and still provide a therapeutically useful combination because of the synergistic therapeutic effect of the drug combination.

As used herein, the terms "synergy" and "synergistic", or the phrase "in a synergistic manner", refer to the interaction of two or more drugs in vitro or in vivo so that their combined effect when administered together is greater than the sum of the effects observed when each is administered individually. That is, the effect of administering the combination of (i) and (ii) as defined above, is greater than the sum of the effects of administering (i) alone and (ii) alone at their prescribed doses.

One aspect the invention encompasses a method of treating one or more symptoms associated with OAB, comprising administering:
(i) a therapeutically effective amount of a beta-3 adrenergic receptor agonist of Formula (I),

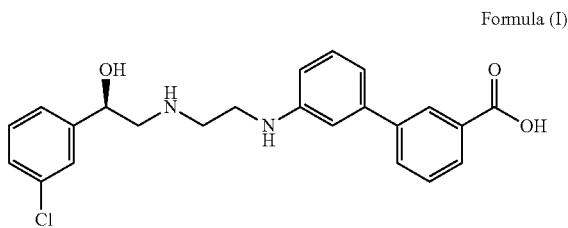 [SMILES: O=C(O)c1cccc(-c2cccc(NCCNC[C@H](O)c3cccc(Cl)c3)c2)c1]

Formula (I)

or pharmaceutically acceptable salts (for example, the hydrochloride salt), pharmaceutically acceptable solvates, or pharmaceutically acceptable salts solvated with pharmaceutically acceptable solvents thereof; and
(ii) a therapeutically effective amount, or a sub-therapeutically effective amount, of a muscarinic receptor antagonist of Formula (II),

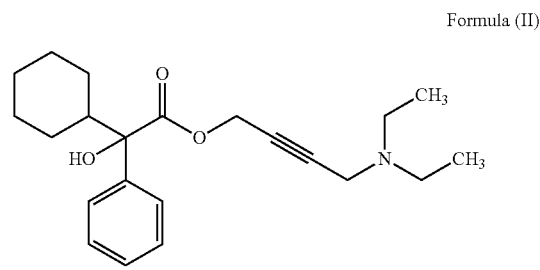 [SMILES: CCN(CC)CC#CCOC(=O)C(O)(c1ccccc1)C1CCCCC1]

Formula (II)

or pharmaceutically acceptable salts, pharmaceutically acceptable solvates, or pharmaceutically acceptable salts solvated with pharmaceutically acceptable solvents thereof.

The compound of Formula (I) has the chemical name 3'-[(2-{[(2R)-2-(3-chlorophenyl)-2-hydroxyethyl] amino}ethyl)-amino]-[1,1'-biphenyl]-3-carboxylic acid, and is known as solabegron. Solabegron can be administered as a salt, which can be anhydrous, hydrated, or solvated with a pharmaceutically acceptable solvent such as ethanol. In a particular embodiment, solabegron is administered as the hydrochloride salt. In a preferred embodiment, solabegron hydrochloride is the anhydrous hydrochloride salt.

The free base, and pharmaceutically acceptable salts, for example, the hydrochloride salt, of solabegron (Formula (I)) can be prepared, for example, according to the procedures disclosed in International Patent Application No. PCT/EP99/03958, filed Jun. 9, 1999, and published as WO 99/65877 on Dec. 23, 1999; International Patent Application No. PCT/GB00/04697, filed Dec. 8, 2000 and published as WO 01/42195 on Jun. 14, 2001; and International Patent Application No. PCT/US01/49355, filed Dec. 17, 2001 and published as WO2006/113649 on Aug. 29, 2002.

In a further embodiment of the invention, when component (I) is solabegron, it can also comprise the primary active human metabolite of solabegron, shown as Formula (III);

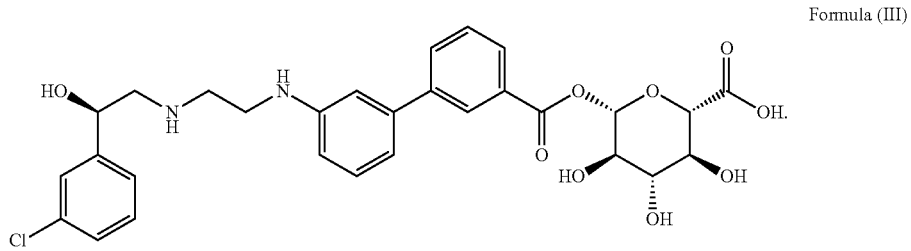 [SMILES: O=C(O[C@@H]1O[C@H](C(=O)O)[C@@H](O)[C@H](O)[C@H]1O)c1cccc(-c2cccc(NCCNC[C@H](O)c3cccc(Cl)c3)c2)c1]

Formula (III)

The compound of Formula (II) has the generic name oxybutynin. The chemical name of the compound of Formula (II) is 4-diethylaminobut-2-ynyl 2-cyclohexyl-2-hydroxy-2-phenyl-ethanoate also known as 4-(diethylamino)-2-butynyl-α-cyclohexyl-α-hydroxybenzeneacetate, also known as 4-(diethylamino)-2-butyn-1-yl-cyclo-hexyl-(hydroxy)phenylacetate. The compound of Formula (II) may be prepared, for example, according to the procedures provided in UK Patent Specification No. GB940,540, filed Jul. 25, 1961, and published on Oct. 30, 1963. The (S) enantiomer of oxybutynin may be prepared according to the procedures in EP 0806948 B1. The (R)-enantiomer of oxybutynin may be prepared according to the procedures in U.S. Pat. No. 6,123,961. Oxybutynin has been proven to be safe and effective in treating patients with overactive bladder and is marketed globally, although side effects are known, vide supra.

In a further embodiment, the invention also encompasses compositions, methods and uses comprising other or additional beta-3 adrenergic receptor agonists, for example, and without limitation, those as taught in International Patent Application No. PCT/EP99/03958, filed Jun. 9, 1999, and published as WO 1999/65877 on Dec. 23, 1999, or for example, Amibegron (SR-58611, Sanofi-Aventis), ritobegron (KUC-7483, Kissel), KRP 204 (N-5984, Kyorin), GS-332 (Mitsubishi Tanabe), YM-178 (Astellas), or the compounds disclosed in US 2011/0028481, published Feb. 3, 2011 (Merck), or those disclosed in US 2012/0157432, published Jun. 21, 2012, now U.S. Pat. No. 8,354,403, published Jan. 15, 2013 (Merck), or those taught in International Patent Publication WO 2009/124167, published Oct. 10, 2009 (Merck), or those disclosed in International Patent Publication WO 2011/025690, published Mar. 3, 2011 (Merck).

One class of other or additional beta-3 adrenergic receptor agonists is represented by the generic structure

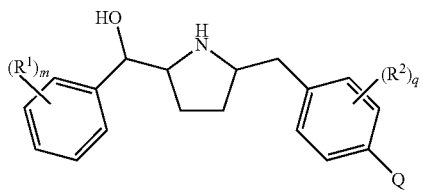

as disclosed in the Merck patents and patent publications listed above. One specific compound has the structure

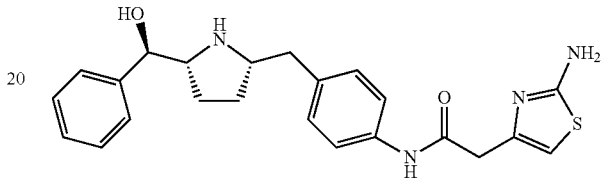

All of the above-mentioned patents and patent applications are incorporated herein by reference in their entireties.

In a further embodiment, suitable muscarinic receptor antagonists other than oxybutynin can also be used according to the present invention. Such antimuscarinics include but are not limited to tolteradine, solifenacin, trospium, darifenacin, propiverine, and fesoterodine.

Accordingly, the invention encompasses treatment combinations comprising (i) a therapeutically effective amount of a beta-3 adrenergic receptor agonist, and (ii) a therapeutically effective amount, or a sub-therapeutically effective amount, of a muscarinic receptor antagonist, the combination being useful for relieving one or more symptoms associated with overactive bladder (OAB) in a synergistic manner, versus the individual components (i) and (ii). The symptoms associated with overactive bladder include, without limitation, frequency of urgency, frequency of mictruitions, nocturia, and urinary incontinence. The combinations of (i) and (ii) of the present invention may be used to treat various combinations of symptoms associated with OAB. Such combinations of OAB symptoms can include, without limitation:

frequency of urgency and nocturia, or
frequency of urgency and urinary incontinence; or
nocturia and urinary incontinence; or
frequency of urgency and nocturia and urinary incontinence; or
frequency of mictruitions and nocturia; or
frequency of mictruitions and frequency of urgency; or
frequency of mictruitions and urinary incontinence; or
frequency of mictruitions and frequency of urgency and nocturia; or
frequency of mictruitions and frequency of urgency and urinary incontinence; or
frequency of mictruitions and nocturia and urinary incontinence; or
frequency of mictruitions and nocturia and urinary incontinence and frequency of urgency.

The invention also encompasses methods of treating one or more symptoms associated with overactive bladder in a mammal using (i) and (ii), either in a single dosage form or separately. Use of the combinations for the treatment of one or more symptoms associated with overactive bladder, use of the combinations in medical therapy, and use of the combinations in the preparation of a medicament for the treatment of one or more symptoms associated with overactive bladder are also embodiments of the present invention.

In one embodiment of the invention, the beta-3 adrenergic receptor agonist comprises a compound selected from the group consisting of solabegron, CL-316,243, mirabegron, pharmaceutically acceptable salts thereof, pharmaceutically acceptable solvates thereof, and pharmaceutically acceptable salts solvated with pharmaceutically acceptable solvents thereof. In a preferred embodiment, the beta-3 adrenergic receptor agonist comprises solabegron, in a total daily oral dose of about 50 to about 800 mg, preferably about 100 to about 500 mg, more preferably about 200 to about 400 mg. In another preferred embodiment, the beta-3 adrenergic receptor agonist comprises mirabegron, in a total daily oral dose of about 25 to about 200 mg, preferably about 25 to about 100 mg, more preferably about 25 to about 50 mg. In yet another preferred embodiment, the beta-3 adrenergic receptor agonist comprises CL-316,243, in a total daily oral dose of about 0.5 to about 500 mg, preferably about 1 to about 100 mg, more preferably about 5 to about 50 mg. These drugs may be administered bis in die (BID), that is twice daily.

In one embodiment of the invention, the muscarinic receptor antagonist comprises a compound selected from the group consisting of oxybutynin, tolterodine, solifenacin, pharmaceutically acceptable salts thereof, pharmaceutically acceptable solvates thereof, and pharmaceutically acceptable salts solvated with pharmaceutically acceptable solvents thereof. In a preferred embodiment, the muscarinic receptor antagonist comprises oxybutynin, in a total daily oral dose of about 1 to about 40 mg, preferably about 1 to about 20 mg, more preferably about 2.5 to about 10 mg. In another preferred embodiment, the muscarinic receptor antagonist comprises tolterodine, in a total daily oral dose of about 1 to about 10 mg, preferably about 1 to about 8 mg, more preferably about 1 to about 4 mg. In still another preferred embodiment, the muscarinic receptor antagonist comprises solifenacin, in a total daily oral dose of about 1 to about 20 mg, preferably about 2.5 to about 15 mg, more preferably about 2.5 to about 10 mg. These drugs may be administered bis in die, that is, twice daily.

In one preferred embodiment the combination comprises (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In one preferred embodiment the combination comprises (i) a therapeutically effective amount of mirabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of mirabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of miragebron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In one preferred embodiment the combination comprises (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

In another preferred embodiment the combination comprises (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof, the combination being useful for relieving one or more symptoms associated with overactive bladder (OAB) in a synergistic manner, versus the individual components (i) and (ii).

Another aspect of the invention is directed to a method of treating one or more symptoms associated with overactive bladder in a mammal, comprising administering to the mammal (i) a therapeutically effective amount of a beta-3 adrenergic receptor agonist; and (ii) a therapeutically effective amount, or a sub-therapeutically effective amount of a muscarinic receptor antagonist.

In one embodiment of the method, the beta-3 adrenergic receptor agonist comprises a compound selected from the group consisting of solabegron, CL-316,243, mirabegron, pharmaceutically acceptable salts thereof, pharmaceutically acceptable solvates thereof, and pharmaceutically acceptable salts solvated with pharmaceutically acceptable solvents thereof. In a preferred embodiment, the beta-3 adrenergic receptor agonist comprises solabegron, in a total daily oral dose of about 50 to about 800 mg, preferably about 100 to about 500 mg, more preferably about 200 to about 400 mg. In another preferred embodiment, the beta-3 adrenergic receptor agonist comprises mirabegron, in a total daily oral dose of about 25 to about 200 mg, preferably about 25 to about 100 mg, more preferably about 25 to about 50 mg. In yet another preferred embodiment, the beta-3 adrenergic receptor agonist comprises CL-316,243, in a total daily oral dose of about 0.5 to about 500 mg, preferably about 1 to about 100 mg, more preferably about 5 to about 50 mg. These drugs may be administered bis in die (BID), that is, twice daily.

In a further embodiment of the method, the muscarinic receptor antagonist comprises oxybutynin, tolterodine, solifenacin, pharmaceutically acceptable salts thereof, pharmaceutically acceptable solvates thereof, and pharmaceutically acceptable salts solvated with pharmaceutically acceptable solvents thereof. In a preferred embodiment, the muscarinic receptor antagonist comprises oxybutynin, in a total daily oral dose of about 1 to about 40 mg, preferably about 1 to about 20 mg, more preferably about 2.5 to about 10 mg. In another preferred embodiment, the muscarinic receptor antagonist comprises tolterodine, in a total daily oral dose of about 1 to about 10 mg, preferably about 1 to about 8 mg, more preferably about 1 to about 4 mg. In still another preferred embodiment, the muscarinic receptor antagonist comprises solifenacin, in a total daily oral dose of about 1 to about 20 mg, preferably about 2.5 to about 15 mg, more preferably about 2.5 to about 10 mg. These drugs may be administered bis in die, that is, twice daily.

In a preferred embodiment, the method of treating one or more symptoms associated with overactive bladder in a mammal, comprises administering to the mammal (i) a therapeutically effective amount of solabegron, or a pharmaceutically acceptable salt, or a pharmaceutically acceptable solvate, or a pharmaceutically acceptable salt solvated with pharmaceutically acceptable solvent thereof, and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of solabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof.

In a preferred embodiment, the method of treating one or more symptoms associated with overactive bladder in a mammal, comprises administering to the mammal (i) a therapeutically effective amount of mirabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of mirabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of mirabegron, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof.

In a preferred embodiment, the method of treating one or more symptoms associated with overactive bladder in a mammal, comprises administering to the mammal (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of tolterodine, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of oxybutynin, or a pharmaceutically acceptable salt, or a pharmaceutically acceptable solvate, or a pharmaceutically acceptable salt solvated with pharmaceutically acceptable solvent thereof.

In another preferred embodiment, the method of treating one or more symptoms associated with overactive bladder in a mammal, comprises administering to the mammal (i) a therapeutically effective amount of CL-316,243, or a pharmaceutically acceptable salt, or a pharmaceutically acceptable solvate, or a pharmaceutically acceptable salt solvated with pharmaceutically acceptable solvent thereof; and (ii) a therapeutically effective amount, or a sub-therapeutically effective amount of solifenacin, or a pharmaceutically acceptable salt, or a pharmaceutically acceptable solvate, or a pharmaceutically acceptable salt solvated with pharmaceutically acceptable solvent thereof.

The methods can comprise co-administration of components (i) and (ii). In one embodiment, components (i) and (ii) are contained in a single or unitary dosage form. In another embodiment, co-administration comprises administering together the separately formulated components (i) and (ii).

The method can also comprise separate administration of components (i) and (ii). When administered separately there can be a time delay between the administration of components (i) and (ii).

In one preferred embodiment, the salt of solabegron comprises the hydrochloride salt.

Another embodiment is directed to a pharmaceutical composition comprising the combination of components (i) and (ii), and further comprising one or more pharmaceutically acceptable carriers, diluents or excipients. One preferred pharmaceutical composition comprises (i) solabegron, or a pharmaceutically acceptable salt, or a pharmaceutically acceptable solvate, or a pharmaceutically acceptable salt solvated with pharmaceutically acceptable solvent thereof, (ii) tolterodine, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients. Another preferred pharmaceutical composition comprises (i) miragebron, or a pharmaceutically acceptable salt, or a pharmaceutically acceptable solvate, or a pharmaceutically acceptable salt solvated with pharmaceutically acceptable solvent thereof, (ii) tolterodine, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients. Another preferred pharmaceutical composition comprises (i) solabegron, or a pharmaceutically acceptable salt, or a pharmaceutically acceptable solvate, or a pharmaceutically acceptable salt solvated with pharmaceutically acceptable solvent thereof, (ii) oxybutynin, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients. Yet another preferred pharmaceutical composition comprises (i) miragebron, or a pharmaceutically acceptable salt, or a pharmaceutically acceptable solvate, or a pharmaceutically acceptable salt solvated with pharmaceutically acceptable solvent thereof, (ii) oxybutynin, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients. Another preferred pharmaceutical composition comprises (i) solabegron, or a pharmaceutically acceptable salt, or a pharmaceutically acceptable solvate, or a pharmaceutically acceptable salt solvated with pharmaceutically acceptable solvent thereof, (ii) solifenacin, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients. Still another preferred pharmaceutical composition comprises (i) miragebron, or a pharmaceutically acceptable salt, or a pharmaceutically acceptable solvate, or a pharmaceutically acceptable salt solvated with pharmaceutically acceptable solvent thereof, (ii) solifenacin, or a pharmaceutically acceptable salt, or a pharmaceutically acceptable solvate, or a pharmaceutically acceptable salt solvated with pharmaceutically acceptable solvent thereof, and (iii) one or more pharmaceutically acceptable carriers, diluents or excipients.

A further embodiment is directed to a method of treating one or more symptoms associated with overactive bladder in a mammal, comprising the step of administering to a mammal in need thereof, a therapeutically effective amount of the above-identified combination of components (i) and (ii), or a pharmaceutical composition thereof.

Another embodiment the method of treatment is directed to a method comprising solabegron, wherein component (i) further comprises the primary in vivo metabolite of solabegron, Formula (III)

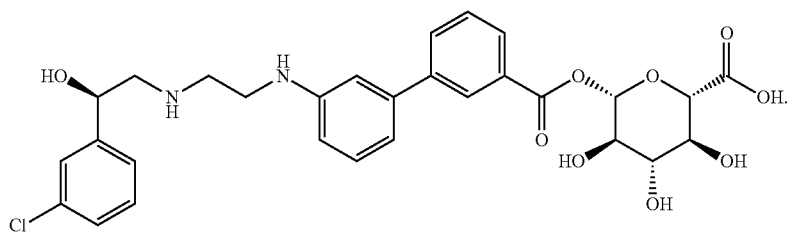

Formula (III)

It is understood that certain embodiments of the invention encompass the use of pharmaceutically acceptable salts, pharmaceutically acceptable solvates, or pharmaceutically acceptable salts solvated with pharmaceutically acceptable solvents, of components (i) and (ii). As used herein, the term "solvate" or "salt solvated", refers to a complex of variable stoichiometry formed by a solute (in this invention, compounds of Formulae (I) or (II) (or a salt thereof)) and a solvent. For the purpose of the present invention, such solvents may not interfere with the biological activity of the solute. Examples of suitable solvents include, but are not limited to, water, methanol, ethanol and acetic acid. In a preferred embodiment, the solvent is a pharmaceutically acceptable solvent. Examples of suitable pharma-ceutically acceptable solvents include, without limitation, water, ethanol and acetic acid. In a more preferred embodiment, the solvent is water, providing a "hydrate".

The beta-3 adrenergic receptor agonist and muscarinic receptor antagonist may be employed in combination by administration concomitantly in (1) a unitary pharmaceutical composition including both compounds (single dosage form) or (2) separate pharmaceutical compositions, where each composition includes one of the compounds. Alternatively, the combination may encompass the separate administration of the compounds in a sequential manner where, for example, either the beta-3 adrenergic receptor agonist or the muscarinic receptor antagonist is administered first and the other compound is administered second. Such sequential administration may be close in time or remote in time, that is, with a time delay.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in a compound of the present invention. Representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexyl-resorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate. N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium and valerate. Other salts, which are not pharma-ceuticaliy acceptable, may also be useful in the preparation of compounds of this invention, and these form a further aspect of the invention.

While it is possible that, for use in medical therapy, the beta-3 adrenergic receptor agonist, muscarinic receptor antagonist, or pharmaceutically acceptable salts, pharmaceutically acceptable solvates, or pharmaceutically acceptable salts solvated with pharmaceutically acceptable solvents thereof, may be administered as the chemical compound itself, the active ingredient or ingredients may also be administered formulated as a pharmaceutical composition. Accordingly, the invention further provides pharmaceutical compositions, which include therapeutically effective amounts of the beta-3 adrenergic receptor agonist, and therapeutically effective amounts, or sub-therapeutically effective amounts, of the muscarinic receptor antagonist, or pharmaceutically acceptable salts, pharmaceutically acceptable solvates, or pharmaceutically acceptable salts solvated with pharmaceutically acceptable solvents thereof, and one or more pharmaceutically acceptable carriers, diluents, or excipients. The carrier(s), diluent(s) or excipient(s) must be acceptable in the sense of being compatible with the other ingredients of the formulation, capable of pharma-ceutical formulation, and not deleterious to the recipient thereof. The invention also provides a process for the preparation of a pharmaceutical formulation including admixing the beta-3 adrenergic receptor agonist, muscarinic receptor antagonist or pharmaceutic-ally acceptable salts, solvates, solvated pharmaceutically acceptable salts thereof, with one or more pharmaceutically acceptable carriers, diluents or excipients.

Pharmaceutical formulations may be presented in unit dose forms containing a predetermined amount of active ingredient per unit dose. As is known to those skilled in the art, the amount of active ingredient per dose will depend on the condition being treated, the route of administration and the age, weight and condition of the patient, or the pharmaceutical formulations may be presented in unit dose forms containing a predetermined amount of active ingredient per unit dose. Preferred unit dosage formulations are those containing a daily dose or sub-dose, or an appropriate fraction thereof, of an active ingredient. Furthermore, such pharmaceutical formulations may be prepared by any of the methods well known in the pharmacy art.

The beta-3 adrenergic receptor agonist and the muscarinic receptor antagonist may be administered by any appropriate route. Suitable routes include oral, rectal, nasal, and parenteral (including intravesical, subcutaneous, intramuscular, intravenous, transdermal, intradermal, intrathecal, and epidural). Administration can also be by means of a bladder pump or sustained release in the bladder.

It will be appreciated that the preferred route may vary with, for example, the condition of the recipient of the combination. It will also be appreciated that each of the agents administered may be administered by the same or different routes and that the beta-3 adrenergic receptor agonist and muscarinic receptor antagonist may be compounded together in a pharmaceutical composition/formulation.

The method of the present invention may also be employed with other therapeutic methods of treating one or more symptoms associated with overactive bladder. Combination therapies according to the present invention thus include the administration of the beta-3 adrenergic receptor agonist and the muscarinic receptor antagonist as well as optional use of other therapeutic agents including other beta-3 adrenergic receptor agonists and/or muscarinic receptor antagonists. Such combination of agents may be administered together or separately and, when administered separately this may occur simultaneously or sequentially in any order, both close and remote in time. The amounts of the compounds of the beta-3 adrenergic receptor agonist and the muscarinic receptor antagonist and the other optional pharmaceutically active agent(s) and the relative timings of administration will be selected in order to achieve the desired combined therapeutic effect.

Further, the combinations and methods of the present invention can comprise isotopes of components (i) and/or (ii), that is, the beta-3 adrenergic receptor agonists and/or muscarinic receptor antagonists are isotopically labeled. In one embodiment, the isotopically labeled compound has one or more hydrogen atoms replaced with either deuterium or tritium. In another embodiment, the isotopically labeled compound has one or more carbon atoms replaced with $^{11}C$, $^{13}C$ or $^{14}C$. In one preferred embodiment, the beta-3 adrenergic receptor agonist comprises deuterated solabegron.

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be used in granulating. The powder mixture can be run through a tablet machine, and if the result is imperfectly formed slugs, they can be broken into granules, and the granules can be lubricated and incorpo-rated back into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethyl-cellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit formulations for oral administration can be microencapsulated. The formulation can also be prepared to prolong or sustain the release as for example, by coating or embedding particulate material in polymers, waxes or the like.

The agents for use according to the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Agents for use according to the present invention may also be delivered by the use of monoclonal antibodies as individual carriers to which the compound molecules are coupled. The compounds may also be coupled with soluble polymers as targetable drug carriers. Such polymers can include, without limitation, polyvinylpyrrolidone, pyran copolymer, polyhydroxypropylmethacrylamide-phenol, polyhydroxyethylaspartamide-phenol, or polyethyleneoxidepolylysine substituted with palmitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for rectal administration may be presented as suppositories or as enemas.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets.

It should be understood that in addition to the ingredients particularly mentioned above, the formulations may include other agents conventional in the art having regard to the type of formulation in question; for example, those suitable for oral administration may include flavoring agents.

Also contemplated in the present invention is a pharmaceutical combination including the beta-3 adrenergic receptor agonist and the muscarinic receptor antagonist. In another embodiment, the pharmaceutical combination includes the beta-3 adrenergic receptor agonist and the muscarinic receptor antagonist and optionally at least one additional beta-3 adrenergic receptor agonist or muscarinic receptor antagonist. The beta-3 adrenergic receptor agonist and the muscarinic receptor antagonist and the additional beta-3 adrenergic receptor agonist or muscarinic receptor antagonist are as described hereinabove.

Therapeutically effective amounts of the beta-3 adrenergic receptor agonist, and therapeutically effective amounts, or sub-therapeutically effective amounts of the muscarinic receptor antagonist, and optionally additional beta-3 adrenergic receptor agonist or muscarinic receptor antagonist are administered to a mammal. Typically, the therapeutically effective amount of one of the administered agents of the present invention will depend upon a number of factors including, for example, the age and weight of the mammal, the precise condition requiring treatment, the severity of the condition, the nature of the formulation, and the route of administration. Ultimately, the therapeutically effective amount will be at the discretion of the attendant physician or veterinarian. Further, a lower dose (sub-therapeutic dose) of the antimuscarinic agent can be administered to provide superior efficacy of the combination while controlling the side effects of the antimuscarinic agent.

The invention encompasses the treatment of any condition that is susceptible to agonism of the beta-3 adrenergic receptor or antagonism of the muscarinic receptor, or a condition that is susceptible to both agonism of the beta-3 adrenergic receptor and antagonism of the muscarinic receptor.

Although not wishing to be bound by any particular theory, it is believed that beta-3 adrenergic receptor agonists, such as solabegron, exert an effect by binding to beta-3 adrenergic receptors, resulting in relaxation of bladder smooth muscle. It is believed that muscarinic receptor antagonists, such as oxybutynin, act via blockade of parasympathetic nerve mediated bladder contraction. That drugs affecting these two different mechanisms of action should provide a synergistic effect, was heretofore both unknown and unexpected.

Examples of conditions associated with over-activity of smooth muscle which are suitable for treatment using a combination comprising the beta-3 adrenergic receptor agonist and the muscarinic receptor antagonist of the present invention include OAB, gastrointestinal syndromes such as irritable bowel syndrome (IBS), inflammatory bowel disease (IBD), ulcerative colitis, and the like. The pharmaceutical combination of the present invention may therefore be effective in the treatment of such conditions. Beta-3 adrenergic receptors have also been found in cardiac tissue. The pharmaceutical combination of the present invention may therefore be effective in the treatment of cardiovascular disease.

The following examples are intended to be illustrative of particular embodiments of the invention, and are not intended to limit the scope of the invention in any way.

EXAMPLES

As used herein the symbols and conventions used in these processes, schemes and examples are consistent with those used in the contemporary scientific literature, for example, the *Journal of the American Chemical Society* and the *Journal of Biological Chemistry*. Unless otherwise noted, all starting materials were obtained from commercial suppliers and used without further purification. Specifically, the following abbreviations may be used in the examples and throughout the specification:

BID twice daily
ECG Electrocardiogram
g (grams) mg (milligrams)
IR immediate release
L (liters) mL (milliliters)
μL (microliters) mol (moles)
M (molar) mM (millimolar)
N (Normal) Kg (kilogram)
mmol (millimoles) RT (room temperature)
min (minutes) h (hours)
QID four times daily
XL extended release Example 1

Drug Interaction Study with Healthy Human Subjects

A drug interaction study was conducted in healthy human volunteers, using repeat oral doses of solabegron and oxybutynin administered singly as well as in combination with each other, in order to assess the effects on pharmacokinetic and pharmacodynamic parameters, as measured by post void residual (PVR) volumes. PVR was measured in subjects treated with each agent alone as well as in combination at steady-state.

The study was a two-cohort randomized, open label, repeat dose, 3-way crossover study in healthy adult subjects. Two marketed formulations of oxybutynin were used in the study: i) Ditropan IR®, which is immediate release (IR) oxybutynin; and ii) Ditropan XL® which is extended release (XL) oxybutynin. The total daily dose given was 20 mg. Solabegron was administered as tablets. Details of the solabegron tablet composition used are provided in Table 1 (composition A).

The first cohort (n=14 subjects) was given solabegron 200 mg BID (100 mg×2) alone for 5 days, this was followed in the second period by oxybutynin IR 5 mg QID alone for 5 days, and in the final dosing period a combination of solabegron 200 mg BID (100 mg×2) with oxybutynin IR 5 mg QID was administered for a period of 5 days.

A second cohort (n=12 subjects) was given solabegron 200 mg BID (100 mg×2) alone for 5 days, this was followed in the second period by oxybutynin XL 10 mg BID alone for 5 days, and in the final dosing period a combination of solabegron 200 mg BID (100 mg×2) with oxybutynin XL 10 mg BID was administered for a 5 day period.

Each study session was separated by a washout period of at least 5 days. Safety assessments included vital signs, ambulatory blood pressure monitoring (ABPM) physical examinations, clinical laboratory safety tests, 12-lead ECGs, PVR volume, to assess the potential for urinary retention, and adverse events. PVR was also utilized as a biomarker of bladder smooth muscle relaxation to determine if solabegron combined with oxybutynin had a greater effect on relaxation than either compound alone in healthy subjects.

Finally, blood samples were collected for pharmacokinetic analysis of plasma concentrations of, as appropriate:
  solabegron and its primary active metabolite as shown hereinbelow;
  R-oxybutynin, S-oxybutynin and the metabolites R-desethyl oxybutynin and S-desethyl oxybutynin as shown hereinbelow.

Primary active metabolite of solabegron, Formula III:

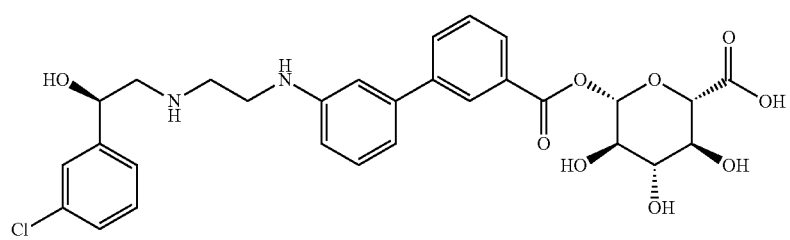

Formula (III)

Primary active metabolite of oxybutynin is desethyloxybutynin, Formula (IV):

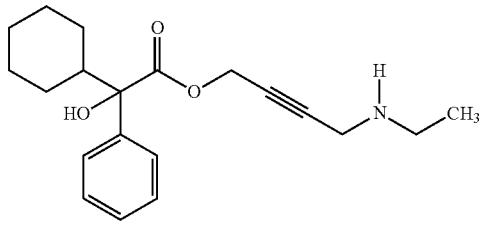

Formula (IV)

Solabegron Tablet Composition A

Composition A was prepared by the blending and wet granulation of ingredients (a) through (e). Table 1, in a suitable high shear mixer/granulator. Ingredients (f) through (h) were added to the dried granulation, blended and compressed. Compressed tablets were covered with an aqueous film coat,

TABLE 1

Composition A

| COMPONENT | UNIT FORMULA (mg) | FUNCTION |
|---|---|---|
| Wet Granulation Ingredients | | |
| (a) GW427353, B, ACTIVE SUBSTANCE | 110* | Active Ingredient |
| (b) MANNITOL 60 | 119.25 | Filler |
| (c) METHYLCELLULOSE, METHOCEL A15 PREMIUM LV | 10 | Binder |
| (d) CROSCARMELLOSE SODIUM | 10 | Disintegrant |
| (e) POLOXAMER F 68 | 2.5 | Surfactant |
| Extra granular Ingredients | | |
| (f) CROSCARMELLOSE SODIUM | 5 | Disintegrant |
| (g) MAGNESIUM STEARATE | 2.5 | Lubricant |
| (h) COLLOIDAL SILICON DIOXIDE | 0.75 | Glidant |
| Total | 250 | |

*100 mg after correction for purity and salt/base conversion.

Results of the Drug Interaction Study—PVR Volume

Bladder ultrasound scans to measure PVR volumes were conducted on Day-1 (one day prior to the dosing period) and Day 6 (sixth day of the dosing period) of each study session.

Subjects dosed with solabegron alone or oxybutynin IR alone showed a mean increase from baseline of 4.4 mL and 45.7 mL in PVR volume respectively, while subjects dosed with the combination of solabegron and oxybutynin IR unexpectedly showed a mean increase from baseline of 79.8 mL. Subjects dosed with oxybutynin XL alone showed a mean increase from baseline of 20.2 mL in PVR volume while subjects dosed with the combination of solabegron and oxybutynin XL unexpectedly showed a mean increase from baseline of 50.8 mL in PVR volume. These data are summarised in Table 2.

TABLE 2

PVR data

| Active ingredient(s) administered | Mean increase from baseline (mL) |
|---|---|
| Solabegron | 4.4 |
| oxybutynin IR | 45.7 |
| oxybutynin XL | 20.2 |
| solabegron and oxybutynin IR | 79.8 |
| solabegron and oxybutynin XL | 50.8 |

These data indicate that in healthy subjects, solabegron given alone showed minimal changes in PVR volumes and oxybutynin IR or XL given alone showed modest changes in PVR volume, but solabegron and either oxybutynin IR or oxybutynin XL given in combination showed greater increases in PVR volumes in each case than is expected from an additive effect of the two active ingredients. When oxybutynin IR is used as the antimuscarinic, the PVR of the combination treatment is 79.8 mL versus 50.1 mL for the PVR sum of the individually administered drugs. Similarly, when oxybutynin XL is used as the antimuscarinic, the PVR of the combination treatment is 50.8 mL versus 24.6 mL for the PVR sum of the individually administered drugs. The latter comparison shows an increase of over 100% for the combination treatment versus the individual treatments.

This is interpreted as evidence of pharmacological synergism in the combination treatment, which indicates increased efficacy in treating one or more of the symptoms of OAB, since retaining more fluid in the PVR test indicates that the bladder muscles are more relaxed, thereby increasing bladder capacity.

Example 2

Effects of the Combination of Beta-Adrenoceptor Agonists and Antimuscarinics on Bladder Contractility in Rats Stimulation of efferent nerves to the urinary bladder results in the release of acetylcholine (ACh) that stimulates post-junctional muscarinic (M3) receptors on urinary bladder smooth muscle, resulting in contraction and subsequent urination. M2 receptors are functionally expressed in human bladder smooth muscle and may also play a role in bladder contractility, however most likely indirectly by enhancing M3 mediated contractions and inhibiting β-adrenoceptor mediated relaxation. Antimuscarinic drugs are believed to work primarily by blocking M3 receptors, thus inhibiting the contractions associated with overactive bladder.

Another approach to treating overactive bladder involves targeting β3-adrenoceptors, which are also located on urinary bladder smooth muscle. The stimulation of post-junctional β3-adrenoceptors results in the generation of cAMP and production of direct relaxation of bladder smooth muscle.

In order to investigate a possible pharmacological synergy on the combination of the muscarinic and the beta receptor pathways, the combination of the muscarinic antagonist oxybutynin and the beta-3 adrenoceptor agonist CL-316,243 (a very selective and potent rodent β3-AR agonist) was tested on EFS (electrical field stimulation)-induced responses in urinary bladder strips from rats.

Longitudinal strips of rat detrusor muscle were suspended in organ bath chambers containing oxygenated Krebs solution (pH 7.4, gassed with 95% $O_2$ and 5% $CO_2$ at 37° C.). Prazosin (1 μM) was added to the Krebs solution in order to block α1-adrenoceptors. Bladder responses were measured using isometric transducers and recorded using a data acquisition system. Tissues were allowed to equilibrate under a resting tension of 1.0 g for 60 min. Following the equilibration period, strips were exposed to KCl (80 mM) to measure their viability. Tissues were washed and equilibrated for another 45 min period. Bladder strips were then subjected to EFS using the following parameters: maximal current 800 mA, frequency of 15 Hz, square pulse of 0.1 ms, trains of 4 s every 2 min. After approximately 15 min (when EFS contractions had stabilized), the selective β2-adrenoceptor antagonist ICI-118551 (30 nM) was incubated for 15 min. After stabilization of the contractile response, a concentration response curve was obtained for each bladder strip by adding CL-316,243 or oxybutynin (1 nM to 10 μM) (or corresponding vehicle) in log unit concentration increments.

In the first series of experiments it was determined that oxybutynin at a concentration of 10 nM produced a minimal (approximately 15% inhibition of EFS-induced bladder strip contraction.

In a second series of experiments, a single concentration of oxybutynin at 10 nM (determined from the first series of experiments) was added to organ bath chambers followed by various doses of CL-316,243 to provide a concentration-response curve for CL-316,243.

In the presence of a minimally effective dose of oxybutynin, there was an approximate 3.5-fold shift to the left of concentration-response curve to CL-316,243. The $EC_{50}$ for inhibiting bladder contraction by CL-316,243 was 7.2 nM; however, in the presence of oxybutynin (10 nM) the $EC_{50}$ was 2.1 nM.

In addition, maximal inhibition of EFS-induced contractions by CL-316,243 alone was 65%, however in the presence of oxybutynin (10 nM) inhibition by CL-316,243 achieved 80% inhibition.

The differences in the $EC_{50}$ values and the inhibition of the maximal response were statistically significant ($p<0.05$).

These data indicate there was significant pharmacological synergy of the efficacy of inhibiting bladder contraction with the combination of an antimuscarinic agent with a selective beta-3 adrenoceptor agonist.

Example 3

Effects of the Combinations of Various Beta-Adrenoceptor Agonists and Antimuscarinics on Rat Bladder Contractions Induced by EFS (Electrical Field Stimulation)

In this study various combinations of β3-adrenoceptor agonists and antimuscarinics were tested in isolated rat urinary bladder strips.

Urinary bladder smooth muscle strips were obtained from female rats (Sprague-Dawley strain, body weight 240-360 g). Two strips per bladder were prepared and connected to tension transducers in 5 ml organ baths containing Krebs-Henseleit solution (kept at 37° C., pH 7.4, gassed with 95% O2/5% CO2). Prazosin (1 μM) was added to the Krebs solution in order to block α1-adrenoceptors. Strips were equilibrated for at least 60 min at 1.0 g resting tension, during which tissues were washed every 15 min. Then, each strip was exposed to 80 mM KCl to verify its viability. After another 45 min wash-out period, strips were subjected to EFS (electrical field stimulation parameters: constant current 800 mA frequency of 15 Hz; square pulse of 0.1 ms, train of 4 s every 2 min). After stabilization, ICI-118,551 (30 nM), a β2-adrenoceptor antagonist, was incubated for 15 min then 10 nM of oxybutynin, tolterodine, solifenacin, or their common solvent (vehicle control) were added to the strips for an additional 15 min. Cumulative concentrations of solabegron (10 nM-10 μM), mirabegron (10 nM-10 μM) and CL-316,243 (1 nM-10 μM) were then added in half-log increments. At the end of CRC's, 10 μM forskolin (FSK) was added to determine maximal relaxation (FIG. 1).

Results are displayed in FIGS. 2-8, and are expressed as % inhibition (mean±SEM) of basal EFS-induced contractions (EFS values obtained 15 min after addition of ICI-118,551).

Each CRC was fit using non-linear regression (GraphPad Prism® software) to obtain Emax and $pIC_{50}$ ($-\log IC_{50}$) values. Mean CRCs for vehicle and treated strips were fit in parallel and statistically compared. The first fit was used to compare $E_{max}$ values and when these values were not statistically different, a second fit was performed, sharing $E_{max}$ in order to obtain $pIC_{50}$ values for each pair of curves. Differences were considered statistically significant when the null hypothesis could be rejected at a risk α of less than 0.05.

As evidenced by the data presented in the Figures, the $E_{max}$ values of CL-316,243 were significantly increased in the presence of oxybutynin and tolterodine. Further, the $IC_{50}$ of CL-316,243 was significantly decreased in the presence of oxybutynin.

For solabegron, the values were significantly increased by oxybutynin, tolterodine and solifenacin. Further, the $IC_{50}$ values of solabegron were significantly lower in the presence of oxybutynin and tolterodine.

For mirabegron, the $E_{max}$ value appeared to be increased in the presence of tolterodine. Further, the $IC_{50}$ values of mirabegron were significantly lower in the presence of oxybutynin, tolterodine and solifenacin.

Thus, it is clear that antimuscarinics can affect both the potency and efficacy of beta-3 adrenergic receptor agonists.

All references cited herein are incorporated herein in their entireties.

What is claimed is:

1. A synergistic combination for relieving one or more symptoms associated with overactive bladder (OAB) comprising:
   (i) a therapeutically effective amount of a beta-3 adrenergic receptor agonist, wherein said beta-3 adrenergic receptor agonist is solabegron, or a pharmaceutically acceptable salt thereof; and
   (ii) a therapeutically effective amount, or a sub-therapeutically effective amount of a muscarinic receptor antagonist, wherein said muscarinic receptor antagonist is oxybutynin, or a pharmaceutically acceptable salt thereof.

2. The combination of claim 1, wherein said one or more symptoms associated with overactive bladder are selected from the group consisting of frequency of urgency, frequency of micturition, nocturia, and urinary incontinence.

3. The combination of claim 1, wherein said therapeutically effective amount of solabegron, or a pharmaceutically acceptable salt thereof is suitable for oral administration.

4. The combination of 1, wherein the salt of solabegron is a hydrochloride salt.

5. The combination of claim 1, wherein said therapeutically effective amount of solabegron, or a pharmaceutically acceptable salt thereof is from 50 to 800 mg.

6. The combination of claim 1, wherein said therapeutically effective amount of solabegron, or a pharmaceutically acceptable salt thereof is from 100 to 500 mg.

7. The combination of claim 1, wherein said therapeutically effective amount of solabegron, or a pharmaceutically acceptable salt thereof is from 200 to 400 mg.

8. The combination of claim 1, wherein said therapeutically effective amount, or a sub-therapeutically effective amount of oxybutynin, or a pharmaceutically acceptable salt thereof is suitable for oral administration.

9. The combination of claim 1, comprising a therapeutically effective amount of oxybutynin, or a pharmaceutically acceptable salt thereof.

10. The combination of claim 9, wherein said therapeutically effective amount of oxybutynin, or a pharmaceutically acceptable salt thereof is from 1 to 40 mg.

11. The combination of claim 9, wherein said therapeutically effective amount of oxybutynin, or a pharmaceutically acceptable salt thereof is from 1 to 20 mg.

12. The combination of claim 9, wherein said therapeutically effective amount of oxybutynin, or a pharmaceutically acceptable salt thereof is from 2.5 to 10 mg.

13. The combination of claim 1, wherein said overactive bladder (OAB) is selected from the group consisting of neurogenic, idiopathic and outlet obstruction.

14. The combination of claim 1, wherein said overactive bladder (OAB) is selected from the group consisting of neurogenic and idiopathic.

15. A pharmaceutical composition comprising the combination of claim 1, further comprising one or more pharmaceutically acceptable carriers, diluents, or excipients.

16. The pharmaceutical composition of claim 15, wherein said pharmaceutical composition is suitable for oral administration.

* * * * *